US005716388A

United States Patent [19]
Petelle

[11] Patent Number: 5,716,388
[45] Date of Patent: Feb. 10, 1998

[54] FLEXIBLE POUCH FOR THERMAL THERAPY PACK

[76] Inventor: Paula A. Petelle, 6019 Thursby Ave., Dallas, Tex. 75252

[21] Appl. No.: 547,652

[22] Filed: Oct. 24, 1995

[51] Int. Cl.$^6$ ...................................................... A61F 7/00
[52] U.S. Cl. .......................... 607/108; 607/112; 607/114; 126/204
[58] Field of Search ..................... 224/575, 576, 224/577, 660, 236, 901.2, 901, 671, 2, 4, 666, 776–779, 235, 661, 662, 224 F, 288 F; 604/345; 907/96, 108–112, 114; 62/530; 383/901; 126/204; 165/45

[56] References Cited

U.S. PATENT DOCUMENTS

| 1,648,565 | 11/1927 | Primley | D3/225 |
|---|---|---|---|
| 4,381,025 | 4/1983 | Schooley | 607/112 |
| 4,411,267 | 10/1983 | Heyman | 221/676 |
| 4,527,566 | 7/1985 | Abare | 607/112 |
| 4,586,506 | 5/1986 | Nagle | 224/240 |
| 5,135,519 | 8/1992 | Helmer | 604/332 |
| 5,269,023 | 12/1993 | Ross | 126/204 |
| 5,353,975 | 10/1994 | Libertucci | 224/662 |
| 5,378,225 | 1/1995 | Chatmen Jr, et al. | 607/108 |

FOREIGN PATENT DOCUMENTS 2104774   3/1983   United Kingdom ................ 224/246

OTHER PUBLICATIONS

Kaz Incorporated —ThermiPaq instructions and label, 1993 (5 sheets).
I.C.E. Down brochure, date unknown (3 sheets).
Chattanooga Group, Inc. Products Catalog, 1992 (9 sheets).

Primary Examiner—Robert L. Nasser
Attorney, Agent, or Firm—Akin, Gump, Strauss, Hauer & Feld, L.L.P.

[57] ABSTRACT

A flexible pouch for containing a heat transfer pack for the application of thermal therapy to a predetermined portion of a person's body. The pouch is formed of a single piece of woven cotton or wool of generally rectangular configuration and folded to form at least two layers of material forming a front part of the pouch and at least one layer forming the rear part of the pouch and defining a pocket therebetween. Opposed side edges of the front and rear parts are sewn together to define the pocket and a flap closure is formed by an integral extension of the rear part. Hook and loop fastener strips may be secured to the outer surface of the front part and along a distal edge of the closure for closing the pocket to contain the heat transfer pack. Opposed elongated straps are attached to the lateral side edges of the pouch and include suitable adjustable connectors at each end for securing the pouch to the wearer's body in selected positions thereon. The pouch is lightweight, flexible and may be easily worn in a flat or rolled condition by a person without restricting physical activity or interfering with the wearing of outer garments, in particular.

7 Claims, 3 Drawing Sheets

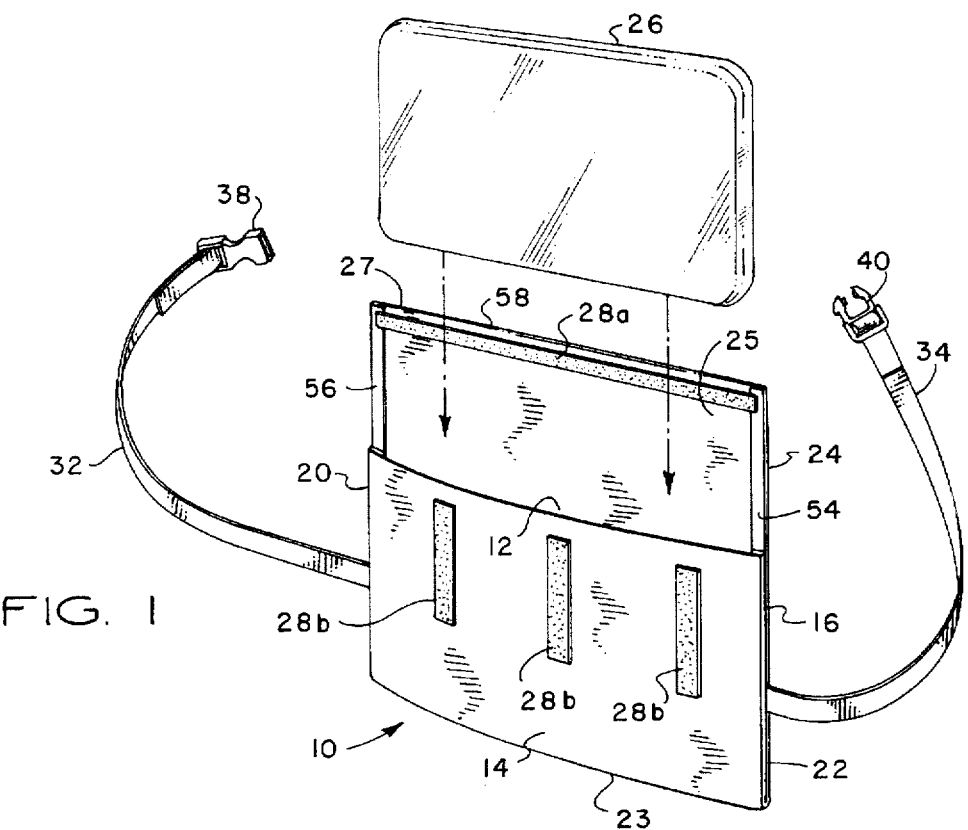
FIG. 1
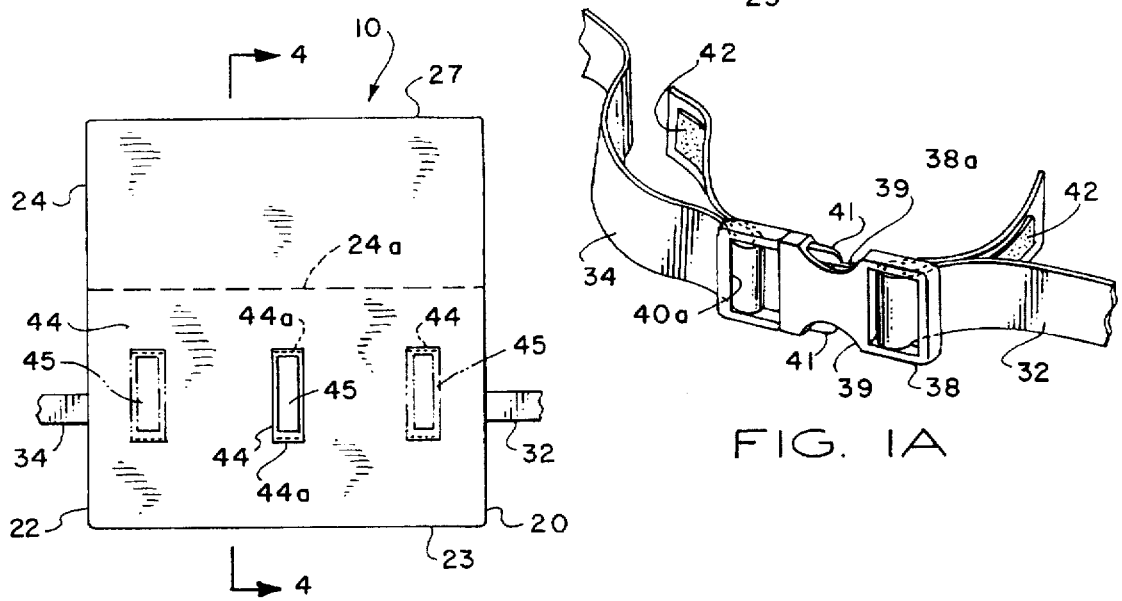
FIG. 2
FIG. 1A

FLEXIBLE POUCH FOR THERMAL THERAPY PACK

FIELD OF THE INVENTION

The present invention pertains to a flexible fabric pouch for holding a heat transfer pack, the pouch including an adjustable strap for attaching the pouch to a selected part of a person's body for the application of thermal therapy.

BACKGROUND

The effectiveness of thermal therapy (hot or cold) to promote healing of various parts of the body has long been recognized. In this regard various devices have been developed which are capable of causing heat transfer to or away from the body to effect therapy. Common ice packs and flexible hot water containers as well as sealed thermal packs which include a quantity of material capable of absorbing heat from or transferring heat to the body have been used extensively. However, one shortcoming of conventional thermal packs of substantially all types is the lack of a suitable holder or pouch which may be conveniently attached to the body without impairing normal physical activity of the user and without being particularly obtrusive if worn over or under conventional clothing, for example. There are many instances wherein thermal therapy, such as for healing of back, shoulder, rib or leg injuries, for example, as well as many other afflictions, can be carried out while the injured person is able to carry on many routine activities. Accordingly, there has been a long-felt need for a suitable holder which may properly contain and apply the thermal pack, whether the pack be merely a bag of ice, a flexible hot water bottle, or one of the flexible thermal packs commercially available, wherein the holder may be easily attached to the body and conform to body contours, be worn over or under conventional articles of outer clothing without discomfort and be easily attached to and detached from the body. It is to these ends that the present invention has been developed.

SUMMARY OF THE INVENTION

The present invention provides a unique holder or pouch for a thermal therapy pack which may be easily worn by the person undergoing therapy and which provides for applying thermal therapy directly to the area of the body requiring same without materially impairing normal physical movement or activity of the person. The holder is lightweight, includes means for easily attaching the holder to and removing the holder from the wearer's body and is relatively unobtrusive so as to permit being worn either over or under normal articles of outer clothing.

In accordance with an important aspect of the invention, a thermal therapy pack holder is provided comprising a flexible pouch formed of a fabric which does not impair heat transfer between a thermal pack disposed in the pouch and the wearer's body and which fabric is also capable of absorbing moisture which may be generated as perspiration by the wearer or as condensation on the thermal pack itself. The pouch is preferably formed of a single piece of fabric which may be folded over to form a relatively flat pocket with a flexible flap closure to permit easy insertion and removal of a thermal pack and to retain the thermal pack during normal activity of the wearer.

In accordance with another important aspect of the invention, a flexible fabric pouch is provided for containing a thermal therapy pack which is relatively flat, lightweight and may be worn attached to various parts of the body without being obtrusive or impairing normal physical activity of the wearer.

In accordance with yet a further aspect of the invention, a flexible pouch is provided for containing a thermal therapy pack and the like which includes a flexible strap and suitable connector means on the strap for rapidly and easily attaching the pouch to and removing the pouch from the wearer's body at the desired location of the pouch for performing therapy on the wearer. The pouch may also be configured as an elongated roll forming a pillow-like member for certain applications such as a lumbar pillow or disposed across the neck or shoulders.

Still further in accordance with the invention, a flexible pouch is provided for containing a thermal therapy pack which is characterized by a relatively flat cloth bag having a pocket for containing a relatively flat flexible thermal therapy pack, a flexible closure or flap for containing the pack in the pouch, adjustable fasteners on the flap and the pouch to permit positioning the flap in a selected closure position for holding the thermal pack in the pouch and opposed straps including quick release connector means disposed at the distal ends of the straps to provide for rapid attachment to and removal of the pouch from the wearer and to provide for quick adjustment of the pouch to prevent unwanted movement of the pouch on the wearer's body. The pouch is preferably made up of a lightweight moisture absorbing fabric such as woven cotton or wool, for example. One side of the pouch may be formed of plural layers of material to provide greater insulation between the thermal pack and the wearer's body. In this way, the pouch may be applied to the body in contact therewith on one or the other sides of the pouch depending on the rate of heat transfer desired between the pouch and the wearer's body.

Those skilled in the art will further appreciate the above-mentioned features and advantages of the invention together with other superior aspects thereof upon reading the detailed description which follows in conjunction with the drawing.

BRIEF DESCRIPTION OF THE DRAWING

FIG. 1 is a perspective view of the flexible pouch type holder for a thermal therapy pack in accordance with the present invention;

FIG. 1A is a detail perspective view of opposed adjustable straps and connectors for the pouch;

FIG. 2 is a rear elevation of the pouch shown in FIG. 1;

DESCRIPTION OF PREFERRED EMBODIMENTS

Figure 3:
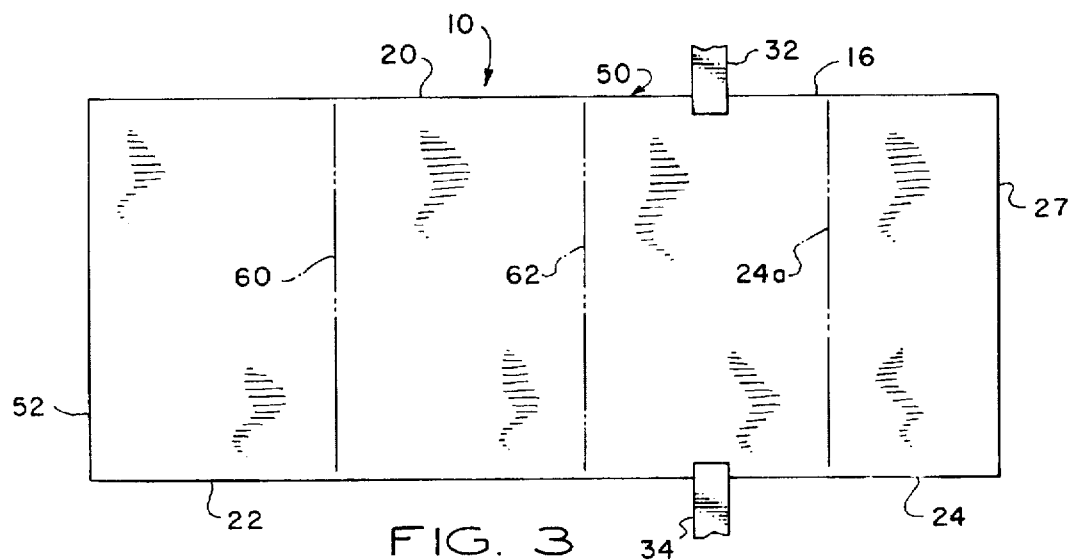
FIG. 3 is a developed plan view of the pouch.

In the description which follows, like elements are marked throughout the specification and drawing with the same reference numerals, respectively. The drawing figures are not necessarily to scale in the interest of clarity and conciseness.

Referring to FIG. 1, a unique flexible pouch for holding a thermal therapy pack is illustrated and generally designated by the numeral 10. The pouch 10 is preferably formed of a single piece of flat woven fabric which is suitably secured to itself to form a generally elongated rectangular pocket 12 defined by a pouch front part 14 and a rear part 16 which are preferably stitched together along opposed generally parallel side edges 20 and 22. The rear part 16 of the pouch 10 is integrally formed with a flexible flap-like closure 24 which may be folded over the pocket 12 to contain a thermal therapy pack therein. FIG. 1 illustrates a typical thermal therapy pack 26 which may be inserted in the pocket 12 and retained therein by the closure 24. The pack 26 may be one of a type commercially available and characterized by a quantity of material having a relatively high capacity for retaining or absorbing heat encased in a flexible plastic sealed envelope, for example. Alternatively, the thermal therapy pack 26 may be simply a waterproof bag of crushed ice or a flexible container for holding a quantity of hot water or other material capable of transferring heat to or from a person's body through the pouch 10.

The closure 24 includes suitable fastening means thereon for engagement with fastening means disposed on the front part 14. For example, the flap closure 24 preferably includes an elongated fastener strip 28a suitably secured to an inside surface 25 thereof between the side edges 20 and 22 and generally adjacent a distal edge 27. The front part 14 of the pouch 10 includes spaced apart elongated fastener strips 28b suitably secured thereto and extending generally parallel to the side edges 20 and 22 and thus normal to the fastener strip 28a. The fastener strips 28a and 28b may comprise hook and loop type fasteners, respectively, such as the type sold under the trademark Velcro, for example. By forming an elongated fastener strip 28a attached to one of the parts such as the closure 24 and providing fastener strips 28b which extend essentially perpendicular to the strip 28a, the position of the distal edge 27 of the flap closure may be varied to accommodate various sizes of thermal therapy packs, such as the pack 26, which may be somewhat larger than the pocket 12.

Referring further to FIGS. 1 and 1A, the pouch 10 is also advantageously provided with means for supporting the pouch at various positions on the body of a person receiving thermal therapy from the therapy pack 26. By way of example, the pouch 10 includes opposed elongated flexible fabric strap members 32 and 34 which are secured to the pouch at and extend normal to the opposed side edges 20 and 22, respectively. The straps 32 and 34 may be formed of a suitable woven polyester fabric, for example. The distal ends of the straps 32 and 34 are trained through opposed quick-release connector members 38 and 40 and the distal ends of the straps 32 and 34 also include respective hook fastener strips 42 suitably secured thereto, FIG. 1A, so that the distal ends of the straps may be secured to the straps themselves to properly train the strap ends, respectively, after the position of the connector members 38 and 40 are adjusted to properly secure the pouch in a preferred position on the wearer's body. The connector 38 is, for example, a generally hollow box-like member having opposed recesses 39 formed therein and the connector 40 has opposed deflectable fingers 41 which are engageable with the connector 42 at the recesses 39 to releasably secure the straps 32 and 34 to each other. The effective length of the straps 32 and 34 is adjusted by the amount of strap end trained through suitable slots 38a and 40a in the respective connectors 38 and 40. The connectors 38 and 40 may be of a type well known to those skilled in the art and commercially available. The opposite ends of straps 32 and 34 are preferably secured to the pouch 10, respectively, between the fabric layers forming the front part 14 and the rear part 16 when the parts are secured to each other to form the pocket 12.

Referring briefly to FIG. 2, the rear part 16 of the pouch 10 is shown provided with one or more fabric belt loops 44 secured thereto such as by conventional thread stitching 44a. If only one belt loop 44 is provided it is preferably centrally located between the opposite side edges 20 and 22 of the pouch and centrally between a lower edge 23 and a fold line 24a which is the normal fold line of the flap closure 24 which will completely close the pocket 12 when the flap is pulled tight. A plurality of loops 44 may be provided on the rear part 16, generally aligned with each other. The belt loops 44 may be used to support the pouch 10 on a wearer's body such as by threading a conventional belt through the loops, particularly if the pouch is to be used to apply thermal therapy to the mid or lower back or the abdominal area of the user. Each belt loop 44 is also preferably provided with a strip of loop fastener 45 extending generally parallel to the longitudinal extent of the loops 44, as shown in FIG. 2, on the outward facing sides of the loops.

Referring now to FIG. 3, the pouch 10 is preferably made from a single piece of fabric material such as a woven cotton canvas, duck, twill or drill. The developed plan view of FIG. 3 shows a single piece of material 50 unhemmed at a transverse edge 52, the edges 20 and 22 and the transverse edge 27. The material piece 50 is of sufficient length that the front part 14 is formed of two layers of material so that it is required to be folded along a fold line 60 to form the front part and then again along a fold line 62 to form the rear part 16. In this way, the pouch 10 is provided with a side comprising the front part 14 which has at least two layers of material while the other side or rear part 16 has only a single layer of material. In this way, the user may place the pouch 10 against the portion of the user's body to receive the thermal therapy wherein the rate of heat transfer between the thermal therapy pack 26 and the person's body is greater or lesser, depending on which side is in contact with the body. If the front part 14 is placed in contact with the body, the flap closure 24 adds even a further layer of material over at least a portion of the surface of the front part 14 which is in contact with the person's body.

In a preferred method of forming the pouch 10, the straps 32 and 34 are placed along the edges of the rear part 16 as shown in FIG. 3, the front part 14 is formed by folding the end of the material piece 50 delimited by the edge 52 along the fold line 60 and then again along the fold line 62 and stitching the front part 14 to the rear part 16 along the edges 20 and 22 with the inner ends of the straps 32 and 34 sandwiched between the front and rear parts substantially midway between lines 62 and 24a. The pocket 12 may then be turned inside out and the side edges 20 and 22 stitched along these edges slightly inset from the first lines of stitching. The pocket is then again turned back to its original configuration to hide all stitching from the pouch exterior. The flap closure 24 may be hemmed at 54, 56 and 58, FIG. 1, before attaching the fastener strip 28a, or while attaching such strip. The material piece 50 is preferably sized to provide a pocket 12 having nominal dimensions of about 8.0 inches by 12.0 inches. The straps 32 and 34 may be about 1.0 inches nominal width. An additional layer of material 53, FIG. 4, such as a nonwoven lightweight polyester may be placed between the layers of material forming the front part 14 prior to folding the material piece 50 along the fold line 60 and so as to give the front part 14 some "body" and minimize slippage between the fabric layers of the front part. The use of cotton canvas duck material has been determined to be advantageous in that the material has good moisture absorbency and insulative properties to prevent heat transfer from the thermal therapy pack to the environment of the wearer while permitting sufficient heat transfer between the pack and the wearer's body to effect proper therapy.

Figure 4:
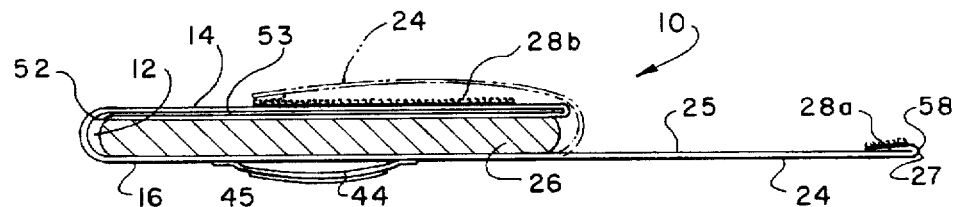
FIG. 4 is a transverse section view of the pouch taken from line 4—4 of FIG. 2.

The section view of FIG. 4 illustrates the therapy pack 26 placed in the pocket 12 so that the flap closure 24 may be folded over and fastened at the hook and loop fasteners 28a and 28b in a selected position of the closure, depending, in part on the size of the pack 26.

Figure 5:
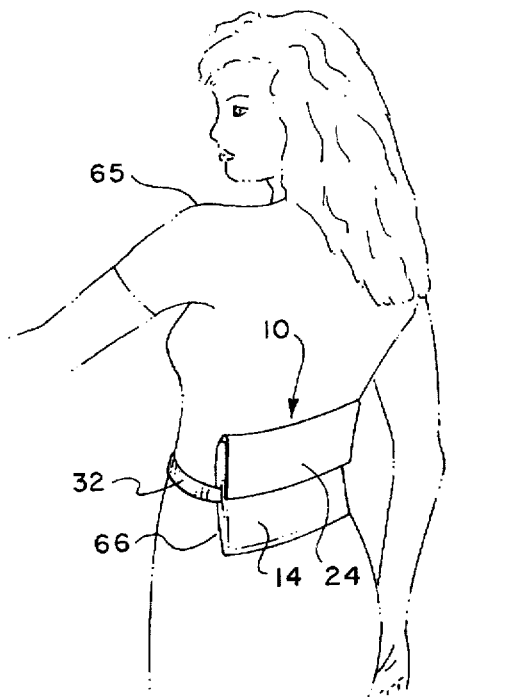
FIG. 5 is a view showing a pouch being worn by a person requiring thermal therapy for the lower back.

Referring to FIG. 5, there is illustrated one position in which the pouch 10 may be worn by a person 65 requiring thermal therapy on the lower back 66. Thanks to the flexible, generally flat pocket formed by the pouch 10, a relatively thin flexible thermal therapy pack 26 may be placed in the pocket and easily conformed to the contour of the body of the wearer to minimize discomfort and enable the wearer to don conventional outer garments which do not interfere with the pouch 10 or vice versa.

Figure 6:
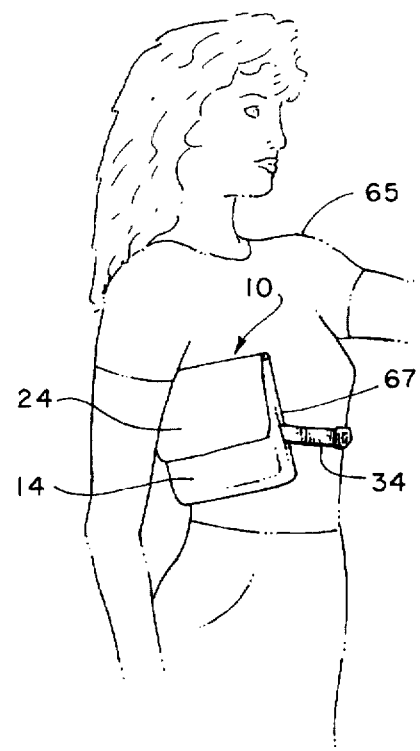
FIG. 6 is a view showing the pouch being worn by a person requiring thermal therapy for the ribs.

Referring to FIG. 6, the pouch 10 is shown being worn by a wearer 65 across an upper portion of the torso to apply thermal therapy to the wearer's rib cage 67, for example. Again, the generally flat, rectangular, flexible nature of the pouch 10 is such to not provide any discomfort or interference with normal physical activity.

Figure 8:
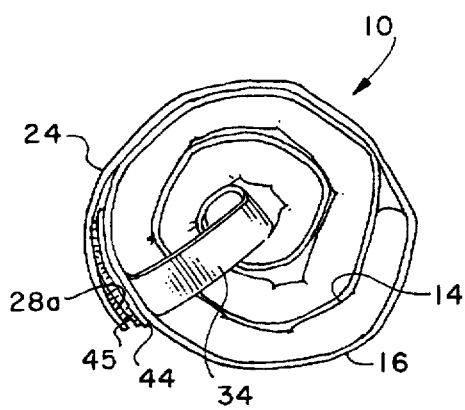
FIG. 8 is a side elevation of the pouch in a rolled and secured position to form a pillow.
Figure 9:
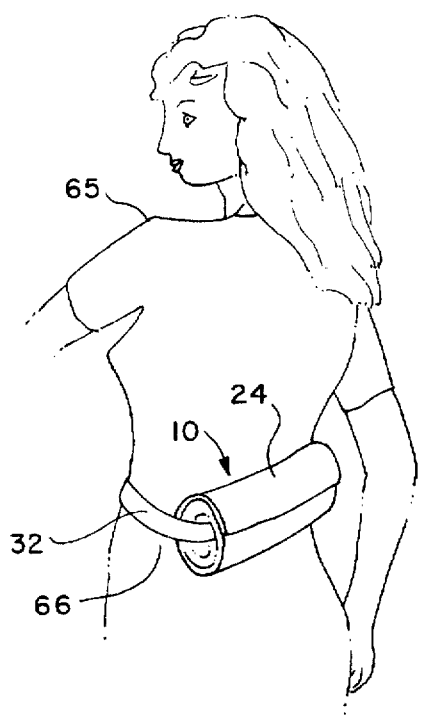
FIG. 9 is a perspective view showing the pouch being worn as a rolled lumbar pillow.

Referring now to FIGS. 8 and 9, the pouch 10 may also be advantageously configured as an elongated pillow-like member with a suitable thermal pack disposed in the pouch in the manner described above. Since the thermal packs intended to be used with the pouch 10 are substantially flexible, the pouch 10 may be rolled into the configuration shown in FIGS. 8 and 9. As shown in FIG. 8, the pouch 10 is rolled in such a way that the front part 14 is inside the rolled configuration of the pouch and the straps 32 and 34 may be tucked into the rolled pouch as illustrated. The pouch 10 may be secured in the rolled condition shown in FIGS. 8 and 9 by attaching the flap closure 24 to the belt loop or loops 44 by engagement of the hook fastener strip 28a with one or more fastener strips 45. Thanks to the arrangement of the fastener strips 45 extending in a direction normal to the longitudinal direction of the fastener strip 28a, the flap closure 24 may be attached to the fastener strips 45 over a relatively wide range of positions to make the pouch roll relatively tight or relatively loose, as desired. In the rolled condition of the pouch 10 shown in FIG. 8, with the straps 32 and 34 tucked within the pouch roll, the pouch may be used as a lumbar pillow or as a neck or shoulder support for applying thermal therapy, for example.

Alternatively, as shown in FIG. 9, the pouch may be worn in the same manner as shown in conjunction with FIG. 5 but in the rolled condition with the straps 32 and 34 extended in their normal working positions. FIG. 9 shows the person 65 wearing the pouch 10 in a rolled configuration to apply thermal therapy to the lower back 66 when both standing or seated. The fastener strips 45 may, of course, be attached to the rear part 16 of the pouch 10 adjacent to the belt loops 44.

Figure 7:
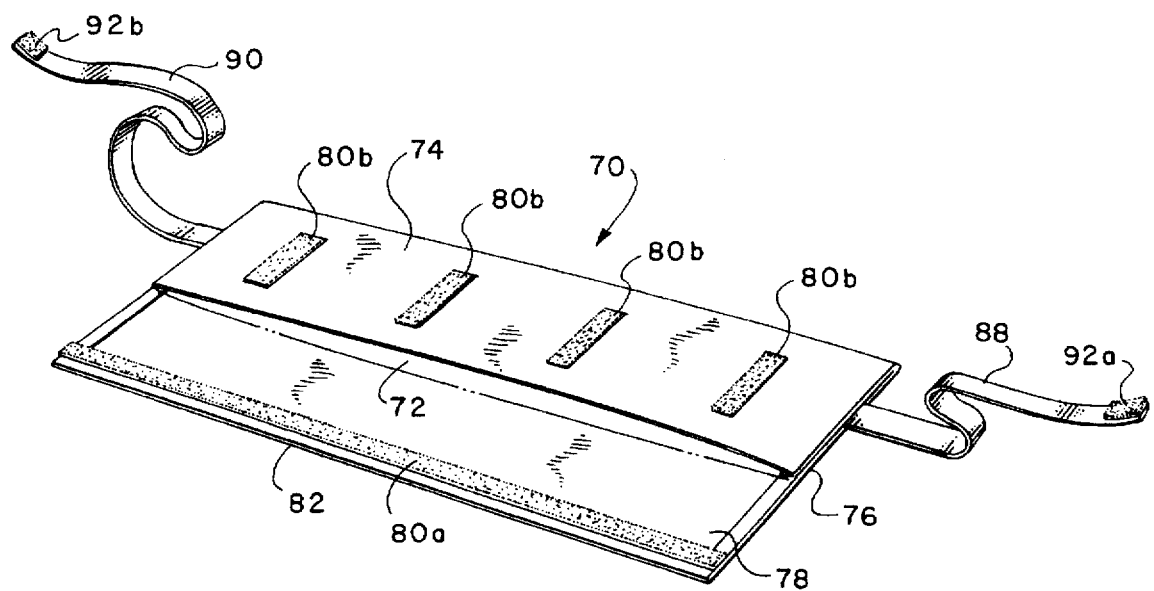
FIG. 7 is a perspective view of an alternate embodiment of the flexible pouch of the present invention.

FIG. 7 is a perspective view of an alternate embodiment of a flexible, thermal therapy pack holder or pouch in accordance with the invention and generally designated by the numeral 70. The pouch 70 is similar in many respects to the pouch 10 and includes a generally elongated, rectangular fabric member forming a pocket 72 delimited by a front part 74 and a rear part 76. The rear part 76 is integral with a flexible flap closure 78 on which an elongated hook fastener strip 80a is sewn adjacent to a distal edge 82 of the closure. Plural loop fastener strips 80b are suitably secured to the front part 74 and are elongated in a direction normal to the fastener strip 80a to provide for adjusting the position of the flap closure 78 in a closed position thereof similar to that described for the flap closure 24. Suitable flexible straps 88 and 90 are secured to the pouch 70 in essentially the same manner as the straps 32 and 34 are secured to the pouch 10. The straps 88 and 90 may be formed with hook fastener strips 92a and 92b suitably secured to the distal ends thereof, respectively, as shown in FIG. 7.

The pouch 70 is advantageous for applying a thermal therapy pack to portions of the body requiring more concentrated application of thermal therapy along a longer and narrower zone or to portions of the body, such as the arms or legs, wherein the pouch may be wrapped completely around the limb and secured by the straps 90 to themselves or to each other using the hook fastener portions 92a and 92b. The pouch 70 may be formed of the same material and in essentially the same manner as the pouch 10 and thus enjoys all of the advantages described herein, and apparent to those skilled in the art, provided by the pouch 10.

Usage of the pouches 10 and 70 by a person requiring thermal therapy in the form of heat transfer to or from the body is believed to be understandable to those of ordinary skill in the art from the foregoing description. The pouches 10 and 70 may be used in veterinary therapy also. Fabrication of the pouches 10 and 70 is also believed to be within the purview of the art worker from the description herein and the accompanying drawings.

Although preferred embodiments of the invention have been described in detail, those skilled in the art will also recognize that various substitutions and modifications may be made without departing from the scope and spirit of the invention as recited in the appended claims.

What is claimed is:

1. In combination, a flexible thermal therapy pack for transferring heat between said thermal therapy pack and a selected portion of a person's body and a flexible pouch for attachment to said body requiring thermal therapy on a selected portion of said body, said pouch supporting said thermal therapy pack therein for transferring heat between said thermal therapy pack and said portion of said body, said pouch comprising:

an elongated, substantially rectangular piece formed of woven fabric, and folded along a first fold line to form a front part of said pouch having plural layers of fabric and folded along a second fold line to define a substantially flat rectangular pocket between said front part and a rear part of said pouch, said thermal therapy pack being disposed in said pocket, said front part and said rear part being sewn together along opposed lateral side edges thereof;

a flap closure comprising a further portion of said piece extending from said rear part and formed integral therewith, said flap closure being foldable to form a closure over an opening to said pocket to retain said thermal therapy pack in said pocket;

cooperating fastener means disposed on said flap closure and on an outer surface of said front part for securing said flap closure to said front part to close said pocket; and elongated strap means connected to said pouch at and extending substantially normal to said opposite side edges, said strap means each including connector means formed thereon for securing said pouch in a predetermined position attached to said body.

2. In combination, a thermal therapy pack operable to provide heat transfer between said thermal therapy pack and a portion of a person's body; and a flexible pouch for containing said thermal therapy pack comprising:

opposed flexible front and rear parts forming a substantially flat pocket therebetween, said thermal therapy pack being disposed in said pocket;

a flexible closure attached to one of said parts and foldable over an opening to said pocket defined between said parts to retain said thermal therapy pack in said pocket;

releasable fastener means on said closure and on the other of said parts for attaching said closure to said other part in a selected position;

opposed, elongated straps secured to opposite sides of said pouch at one end thereof, respectively, the opposite ends of said straps including connector means for connecting said straps to each other to secure said pouch to a person's body for application of thermal therapy thereto; and at least one belt loop secured to one of said parts of said pouch for training a belt therethrough to support said pouch on said person's body.

3. The pouch set forth in claim 2 including:

fastener means disposed on an outer side of said one belt loop for engagement with said fastener means on said closure in a rolled configuration of said pouch for securing said pouch in said rolled configuration to form a pillow-like member.

4. In combination, a thermal therapy pack operable to provide heat transfer between said thermal therapy pack and a portion of a person's body; and a flexible pouch for containing said thermal therapy pack comprising:

opposed flexible front and rear parts forming a substantially flat pocket therebetween, said thermal therapy pack being disposed in said pocket;

a flexible closure attached to one of said parts and foldable over an opening to said pocket defined between said parts to retain said thermal therapy pack in said pocket;

releasable fastener means on said closure and on the other of said parts for attaching said closure to said other part in a selected position;

opposed, elongated straps secured to opposite sides of said pouch at one end thereof, respectively, the opposite ends of said straps including connector means for connecting said straps to each other to secure said pouch to a person's body for application of thermal therapy thereto; and fastener means supported by said rear part and cooperable with said fastener means on said closure for securing said pouch in a rolled configuration to form a pillow-like member for application of thermal therapy to said person's body.

5. In combination, a thermal therapy pack and a flexible pouch for containing said thermal therapy pack to provide heat transfer between said thermal therapy pack and a portion of a person's body, said pouch comprising:

opposed flexible front and rear parts forming a substantially flat pocket therebetween, said thermal therapy pack being disposed in said pocket;

a flexible closure attached to one of said parts and foldable over an opening to said pocket defined between said parts to retain said thermal therapy pack in said pocket;

releasable fastener means on said closure and on the other of said parts for attaching said closure to said other part in a selected position;

opposed, elongated straps secured to opposite sides of said pouch at one end thereof, respectively, the opposite ends of said straps including connector means for connecting said straps to each other to secure said pouch to a person's body for application of thermal therapy thereto; and said pouch comprising a single piece of fabric wherein said front part comprises at least two layers of fabric formed by said single piece of fabric folded at first and second spaced apart fold lines and said rear part is formed of fewer layers of fabric than said front part and is formed by said single piece of fabric folded at said second fold line, and said front part and said rear part are secured to each other along opposed side edges thereof, respectively, and said closure is formed by an integral extension of said rear part.

6. In combination, a thermal therapy pack operable to provide heat transfer between said thermal therapy pack and a portion of a person's body; and a flexible pouch for containing said thermal therapy pack comprising opposed flexible front and rear parts forming a substantially flat pocket therebetween, said thermal therapy pack being disposed in said pocket;

a flexible closure attached to one of said parts and foldable over an opening to said pocket defined between said parts for retaining said thermal therapy pack in said pocket;

releasable fastener means on said closure and on the other of said parts for attaching said closure to said other part in a selected position; and opposed, elongated straps secured to opposite sides of said pouch at one end thereof, respectively, the opposite ends of said straps each including connector means for connecting said straps to each other to secure said pouch to a person's body for application of thermal therapy thereto, and fastener means on said straps comprising a fastener strip attached to each of said straps, respectively, at a distal end thereof for securing said straps to at least one of each of said straps, respectively, and to the other of said straps.

7. The invention set forth in claim 6 wherein:

said straps are trained through slots in each of said connector means, respectively, for adjusting the effective lengths of said straps.

\* \* \* \* \*